United States Patent [19]
Patchett et al.

[11] Patent Number: 6,043,026
[45] Date of Patent: *Mar. 28, 2000

[54] COMBINATION THERAPY FOR THE PREVENTION AND TREATMENT OF OSTEOPOROSIS

[75] Inventors: Arthur A. Patchett, Westfield, N.J.; Gideon A. Rodan, Bryn Mawr, Pa.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/071,211

[22] Filed: May 1, 1998

Related U.S. Application Data

[60] Provisional application No. 60/045,290, May 1, 1997.

[51] Int. Cl.[7] ............................... C12Q 1/00; A61K 51/00
[52] U.S. Cl. .................................. 435/4; 435/6; 424/520; 424/1.45; 424/9.1; 530/399; 552/502
[58] Field of Search ........................... 435/4, 6; 424/520, 424/1.45, 9.1; 530/399; 552/502

[56] References Cited

U.S. PATENT DOCUMENTS

| | | | |
|---|---|---|---|
| 5,118,667 | 6/1992 | Adams et al. | 435/4 |
| 5,457,117 | 10/1995 | Black et al. | 530/399 |
| 5,492,916 | 2/1996 | Morriello et al. | 435/4 |
| 5,494,929 | 2/1996 | Grese | 435/4 |
| 5,534,527 | 7/1996 | Black et al. | 530/399 |
| 5,536,716 | 7/1996 | Chen et al. | 435/4 |
| 5,550,134 | 8/1996 | Audia et al. | 435/4 |
| 5,767,124 | 6/1998 | Draper et al. | 435/4 |

FOREIGN PATENT DOCUMENTS

| | | |
|---|---|---|
| 0 693 285 | 1/1996 | European Pat. Off. . |
| 0 716 855 | 6/1996 | European Pat. Off. . |
| 0 747 056 | 12/1996 | European Pat. Off. . |
| 0 792 640 | 9/1997 | European Pat. Off. . |
| 9511029 | 4/1995 | WIPO . |
| WO 97/24369 | 7/1997 | WIPO . |
| WO 97/31640 | 9/1997 | WIPO . |
| WO 97/46252 | 12/1997 | WIPO . |
| 9825623 | 6/1998 | WIPO . |

*Primary Examiner*—Louise N. Leary
*Attorney, Agent, or Firm*—J. Eric Thies; David L. Rose

[57] ABSTRACT

The combination of an estrogen receptor modulator and a growth hormone secretagogue is useful in the treatment or prevention of diseases involving bone resorption, especially osteoporosis.

21 Claims, No Drawings

COMBINATION THERAPY FOR THE PREVENTION AND TREATMENT OF OSTEOPOROSIS

This application is based on provisional application 60/045,290, filed May 1, 1997.

FIELD OF THE INVENTION

The present invention provides a combination therapy for the treatment and prevention of osteoporosis. More particularly, the combination of the present invention comprises an estrogen receptor modulator and a growth hormone secretogogue.

BACKGROUND OF THE INVENTION

Osteoclasts are multinucleated cells of up to 400 μm in diameter that resorb mineralized tissue, chiefly calcium phosphate, in vertebrates. They are actively motile cells that migrate along the surface of bone. They can bind to bone, secrete necessary acid and proteases and thereby cause the actual resorption of mineralized tissue from the bone.

More specifically, osteoclasts are believed to exist in at least two physiological states. In the secretory state, osteoclasts are flat, attach to the bone matrix via a tight attachment zone (sealing zone), become highly polarized, form a ruffled border, and secrete lysosomal enzymes and acid to resorb bone. The adhesion of osteoclasts to bone surfaces is an important initial step in bone resorption. In the migratory or motile state, the osteoclasts migrate across bone matrix and do not take part in resorption until they attach again to bone.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, loosening of bone prostheses and glucocorticoid treatment.

All these conditions are characterized by bone loss, resulting from an imbalance between bone resorption (breakdown) and bone formation, which continues throughout life at the rate of about 10% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

The literature discloses a variety of estrogen receptor modulators (termed "atypical estrogen agonists", "estrogen receptor mixed agonists/antagonists", "estrogen mimetics", "bone selective estrogens", "antiestrogens", etc.) which are useful in the treatment and prevention of diseases involving bone resorption. Representative examples may be found in the following: U.S. Pat. No. 3,274,213; U.S. Pat. No. 4,133,814; U.S. Pat. No. 4,230,862; U.S. Pat. No. 4,323,707; U.S. Pat. No. 4,380,635; U.S. Pat. No. 4,400,543; U.S. Pat. No. 4,418,068; U.S. Pat. No. 4,536,516; U.S. Pat. No. 5,254,594; EPO Patent Pub. No. 0,062,503; EPO Patent Pub. No. 0,054,168; EPO Patent Pub. No. 0,260,066; EPO Patent Pub. No. 0,470,310; EPO Patent Pub. No. 0,651,998-0,652,005; EPO Patent Pub. No. 0,657,162; EPO Patent Pub. No. 0,659,411-0,659,429; EPO Patent Pub. No. 0,662,325; EPO Patent Pub. No. 0,663,209; EPO Patent Pub. No. 0,664,121-0,664,126; EPO Patent Pub. No. 0,665,015; EPO Patent Pub. No. 0,668,075; EPO Patent Pub. No. 0,670,162; EPO Patent Pub. No. 0,674,903; EPO Patent Pub. No. 0,683,170; EPO Patent Pub. No. 0,703,228; EPO Patent Pub. No. 0,716,855; EPO Patent Pub. No. 0,729,951; EPO Patent Pub. No. 0,729,956; EPO Patent Pub. No. 0,731,093; EPO Patent Pub. No. 0,731,098; EPO Patent Pub. No. 0,731,100; EPO Patent Pub. No. 0,733,620; EPO Patent Pub. No. 0,747,054; German Patent Pub. No. DE 2,329,201; Japan Patent Pub. No. 5,032,579; PCT Patent Pub. No. 96/09039; PCT Patent Pub. No. 96/09040; PCT Patent Pub. No. 96/09041; PCT Patent Pub. No. 96/09045; PCT Patent Pub. No. 96/09050; PCT Patent Pub. No. 96/09051; PCT Patent Pub. No. 96/09052; PCT Patent Pub. No. 96/21441; PCT Patent Pub. No. 96/22771; PCT Patent Pub. No. 96/26727; PCT Patent Pub. No. 96/26935; PCT Patent Pub. No. 96/32937; PCT Patent Pub. No. 96/39833; and Jones, et al., *J. Med. Chem.*, 27 1057–1066 (1984). The preparation of estrogen receptor modulators is well known in the art. Representative examples may be found in the above mentioned references which disclose the compounds as being useful for the treatment of bone diseases, in particular, as inhibitors of bone resorption.

The treatment of osteoporosis with calcitonin, alone and in combination with human growth hormone ("GH") was examined by Aloia, et al., *Metabolism*, 34(2) 124–129 (1985). This publication ascribes no benefit in the treatment of osteoporosis from combining calcitonin therapy with the administration of growth hormone and noted that the addition of growth hormone to calcitonin therapy appeared to have a deleterious effect on cortical bone mass. The effects of growth hormone itself in the treatment of osteoporosis was studied by Aloia, et al., *J. Clin. Endocrinol. Metab.*, 54, 992–999 (1976). This publication noted that under the conditions of the study, growth hormone administration did not result in an increment in skeletal mass. The effects of growth hormone on human bone biology have been reviewed by Inzucchi, et al. *J. Clin. Endocrinol. Metab.*, 79(3), 691–694 (1994). General reviews of human growth hormone also discuss the role of growth hormone on bone (Strobl, et al *Pharmacol. Reviews*, 46(1), 1–34 (1994); Chipman, *J. Pediatric Encocrinol.*, 6(3–4), 325–328 (1993)). Bone turnover and bone mineral density in young adult patients with panhypopituitarism following long-term growth hormone therapy was examined by Balducci, et al. *Eur. J. Endocrinol.*, 132(1), 42–46 (January 1995). Also, the effect of growth hormone replacement on bone has been examined in boys with and without classic growth hormone deficiency (Zadik, et al., *J. Pediatrics*, 125(2), 189–195 (1994)) and in adults with adult onset growth hormone deficiency (Holmes, et al., *Clin. Endocrinol.*, 42, 627–633 (1995)). There is a difference in the literature between effects in GH-deficient children, where improvement with GH is seen, and in adults, where most reports show both, increased bone resorption and formation, but no positive balance.

Certain non-peptidal growth hormone secretagogues are known to stimulate the pituitary gland to increase its secretion of growth hormone with utility in growth hormone deficient children and adults, in severe burn victims, in the treatment of Turners syndrome, for reversing the adverse effects of glucocorticoid treatment, for treating muscle and exercise tolerance deficiencies in growth hormone deficient adults, and for the treatment of osteoporosis. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (J. Endocrinol Invest., 15(Suppl 4), 45 (1992)). Other compounds possessing growth hormone secretagogue activity are disclosed in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; Science, 260, 1640–1643 (Jun. 11, 1993); Ann. Rep. Med. Chem., 28,177–186 (1993); Bioorg. Med. Chem. Ltrs., 4(22),2709–2714 (1994); and Proc. Natl. Acad. Sci. USA 92 7001–7005 (July 1995).

SUMMARY OF THE INVENTION

The present invention provides a combination for the treatment and prevention of diseases involving bone resorption, such as osteoporosis, which comprises an estrogen receptor modulator and a growth hormone secretagogue.

In a preferred embodiment of the invention is the combination wherein the estrogen receptor modulator is selected from the group consisting of: raloxifene, BE-25327, CP-336156, clometherone, delmadinone, droloxifene, idoxifene, nafoxidine, nitromifene, ormeloxifene, tamoxifene, toremifene, trioxifene and ([2-(4-hydroxyphenyl)-6-hydroxynaphthalen-1-yl][4-[2-(1-piperidinyl)-ethoxy) phenyl]-methane.

In a preferred embodiment of the invention is the combination wherein the growth hormone secretagogue is of the Formula I or II:

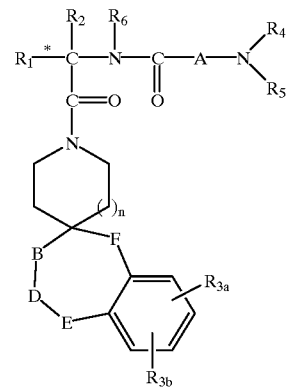

Formula I

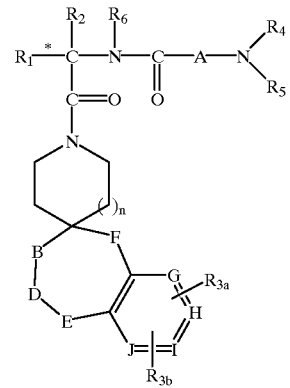

Formula II wherein:
R$_1$ is selected from the group consisting of:
-C$_1$–C$_{10}$ alkyl, -aryl, aryl-(C$_1$–C$_6$ alkyl)-,
C$_3$–C$_7$ cycloalkyl-(C$_1$–C$_6$alkyl)-, -C$_1$–C$_5$alkyl-K-C$_1$–C$_5$alkyl, aryl(C$_0$–C$_5$alkyl)-K-(C$_1$–C$_5$ alkyl)-, and
C$_3$–C$_7$ cycloalkyl(C$_0$–C$_5$ alkyl)-K-(C$_1$–C$_5$ alkyl)-,
wherein K is O, S(O)$_m$, N(R$_2$)C(O), C(O)N(R$_2$), OC(O), C(O)O, or —CR$_2$═CR$_2$—, or —C≡C—,
and wherein the aryl groups are as defined below and the R$_2$ and alkyl groups may be further substituted by 1 to 9 halogen, S(O)mR$_{2a}$, 1 to 3 OR$_{2a}$, or C(O)OR$_{2a}$, and the aryl groups may be further substituted by phenyl, phenoxy, halophenyl, 1–3 C$_1$–C$_6$ alkyl, 1 to 3 halogen, 1 to 2—OR$_2$, methylenedioxy, —S(O)$_m$R$_2$, 1 to 2—CF$_3$, —OCF$_3$, nitro, —N(R$_2$)(R$_2$), —N(R$_2$)C(O)R$_2$, —C(O)OR$_2$, —C(O)N(R$_2$)(R$_2$), —SO$_2$N(R$_2$)(R$_2$), —N(R$_2$)S(O)$_2$ aryl, and —N(R$_2$)SO$_2$R$_2$;

R$_2$ is selected from the group consisting of:
hydrogen, C$_1$–C$_6$ alkyl, C$_3$–C$_7$ cycloalkyl, and where two C$_1$–C$_6$ alkyl groups are present on one atom, they may be optionally joined to form a C$_3$–C$_8$ cyclic ring optionally including oxygen, sulfur or NR$_{2a}$;

R$_{2a}$ is hydrogen, or C$_1$–C$_6$ alkyl;

R$_{3a}$ and R$_{3b}$ are independently selected from the group consisting of: hydrogen, halogen, —C$_1$–C$_6$ alkyl, —OR$_2$, cyano, —OCF$_3$, methylenedioxy, nitro, —S(O)$_m$R, —CF$_3$ or —C(O)OR$_2$ and when R$_{3a}$ and R$_{3b}$ are in an ortho arrangement, they may be joined to form a C$_5$ to C$_8$ aliphatic or aromatic ring optionally including 1 or 2 heteroatoms selected from oxygen, sulfur or nitrogen;

R$_4$ and R$_6$ are independently selected from the group consisting of: hydrogen, —C$_1$–C$_6$ alkyl, substituted $C_1$–$C_6$ alkyl wherein the substituents are selected from 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, —S(O)$_m$($C_1$–$C_6$ alkyl); or $R_4$ and $R_5$ can be taken together to form —(CH$_2$)$_r$L$_a$(CH$_2$)$_s$— where L$_a$ is —C(R$_2$)$_2$—, —O—, —S(O)$_m$—, or —N(R$_2$)—, where r and s are independently 1 to 3 and $R_2$ is as defined above;

$R_6$ is hydrogen or $C_1$–$C_6$ alkyl;

A is:

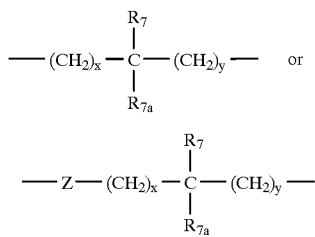

wherein x and y are independently 0–3;

Z is N-$R_2$ or O;

$R_7$ and $R_{7a}$ are independently selected from the group consisting of: hydrogen, —$C_1$–$C_6$ alkyl, —OR$_2$, trifluoromethyl, phenyl, substituted $C_1$–$C_6$ alkyl where the substituents are selected from imidazolyl, phenyl, indolyl, p-hydroxyphenyl, —OR$_2$, 1 to 3 fluoro, —S(O)mR$_2$, —C(O)OR$_2$, —$C_3$–$C_7$ cycloalkyl, —N(R$_2$)(R$_2$), —C(O)N(R$_2$)(R$_2$); or $R_7$ and $R_{7a}$ can independently be joined to one or both of $R_4$ and $R_5$ groups to form alkylene bridges between the terminal nitrogen and the alkyl portion of the $R_7$ or $R_{7a}$ groups, wherein the bridge contains 1 to 5 carbons atoms;

B, D, E, and F are independently selected from the group consisting of: —C(R$_8$)(R$_{10}$)—, —O—, C=O, —S(O)$_m$—, or —NR$_9$-, such that one or two of B, D, E, or F may be optionally absent to provide a 5, 6, or 7 membered ring; and provided that B, D, E and F can be —C(R$_8$)(R$_{10}$)— or C=O only when one of the remaining B, D, E and F groups is simultaneously —O—, —S(O)$_m$—, or —NR$_9$-, or B and D, or D and E taken together may be —N=CR$_{10}$— or —CR$_{10}$=N—, or B and D, or D and E taken together may be —CR$_8$=CR$_{10}$-, provided one of the other of B and E or F is simultaneously —O—, —S(O)$_m$—, or —NR$_9$-;

$R_8$ and $R_{10}$ are independently selected from the group consisting of: hydrogen, —$R_2$, —OR$_2$, (—CH$_2$)$_q$-aryl, —(CH$_2$)$_q$—C(O)OR$_2$, —(CH$_2$)$_q$-C(O)O(CH$_2$)$_q$-aryl, or —(CH$_2$)$_q$-(1H-tetrazol-5-yl), where the aryl may be optionally substituted by 1 to 3 halo, 1 to 2 $C_1$–$C_8$ alkyl, 1 to 3—OR$_2$ or 1 to 2—C(O)OR$_2$;

$R_9$ is selected from the group consisting of: —R$_2$, —(CH$_2$)$_q$-aryl, —C(O)R$_2$, —C(O)(CH$_2$)$_q$-aryl, —SO$_2$R$_2$, —SO$_2$(CH$_2$)$_q$-aryl, —C(O)N(R$_2$)(R$_2$), —C(O)N(R$_2$)(CH$_2$)$_q$-aryl, —C(O)OR$_2$, 1-H-tetrazol-5-yl, —SO$_3$H, —SO$_2$NHC≡N, —SO$_2$N(R$_2$)aryl, —SO$_2$N(R$_2$)(R$_2$), and wherein the (CH$_2$)$_q$ may be optionally substituted by 1 to 2 $C_1$–$C_4$ alkyl, and the $R_2$ and aryl may be optionally further substituted by 1 to 3—OR$_{2a}$, —O(CH$_2$)$_q$ aryl, 1 to 2—C(O)OR$_{2a}$, 1 to 2—C(O)O(CH$_2$)$_q$ aryl, 1 to 2—C(O)N(R$_{2a}$)(R$_{2a}$), 1 to 2—C(O)N(R$_{2a}$)(CH$_2$)$_q$ aryl, 1 to 5 halogen, 1 to 3 $C_1$–$C_4$ alkyl, 1,2,4-triazolyl, 1-H-tetrazol-5-yl, —C(O) NHSO$_2$R$_{2a}$, —S(O)$_m$R$_{2a}$, —C(O)NHSO$_2$(CH$_2$)$_q$-aryl, —SO$_2$NHC≡N, —SO$_2$NHC(O)R$_{2a}$, —SO$_2$NHC(O)(CH$_2$)$_q$ aryl, —N(R$_2$)C(O)N(R$_{2a}$)(R$_{2a}$), —N(R$_{2a}$)C(O) N(R$_{2a}$)(CH$_2$)$_q$-aryl, —N(R$_{2a}$)C(O)(R$_{2a}$), —N(R$_{2a}$)C(O)R$_{2a}$, —N(R$_{2a}$)C(O)(CH$_2$)$_q$ aryl, —OC(O)N(R$_{2a}$)(R$_{2a}$), —OC(O)N(R$_{2a}$)(CH$_2$)$_q$ aryl, —SO$_2$(CH$_2$)$_q$CONH-(CH$_2$)wNHC(O)R$_{11}$, wherein w is 2–6 and $R_{11}$ may be biotin, aryl, or aryl substituted by 1 or 2 OR$_2$, 1–2 halogen, azido or nitro;

m is 0, 1 or 2;

n is 1, or 2;

q may optionally be 0, 1, 2, 3, or 4; and

G, H, I and J are carbon, nitrogen, sulfur or oxygen atoms, such that at least one is a heteroatom and one of G, H, I or J may be optionally missing to afford a 5 or 6 membered heterocyclic aromatic ring;

and pharmaceutically acceptable salts and individual diastereomers thereof.

In a class of the invention is the combination wherein the growth hormone secretagogue is of the Formula V:

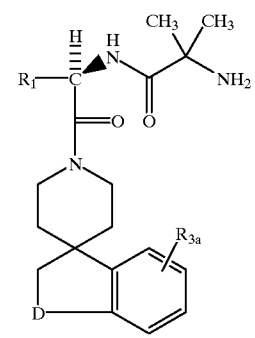

V wherein:

$R_1$ is selected from the group consisting of:

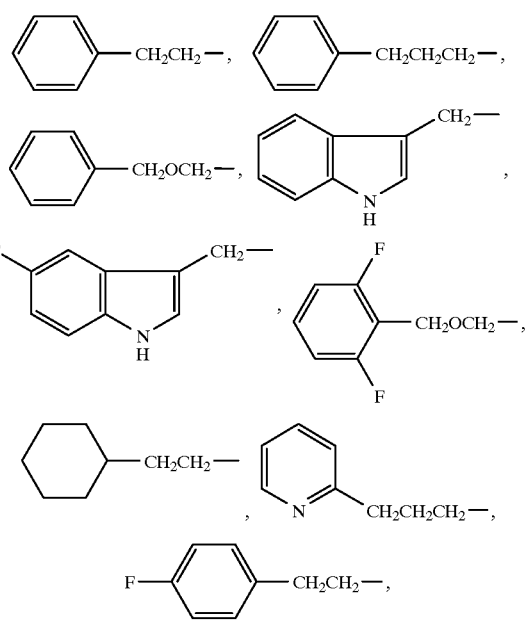

-continued

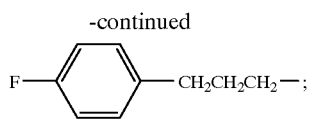

$R_{3a}$ is H, or fluoro;

D is selected from the group consisting of:
—O—, —S—, —S(O)$_m$—, N(R$_2$), NSO$_2$(R$_2$), NSO$_2$(CH$_2$)$_t$aryl, NC(O)(R$_2$), NSO$_2$(CH$_2$)$_q$OH, NSO$_2$(CH$_2$)$_q$COOR$_2$, NSO$_2$(CH$_2$)$_q$C(O)—N(R$_2$) (R$_2$), N—SO$_2$(CH$_2$)$_q$C(O)—N(R$_2$)(CH$_2$)$_w$OH,

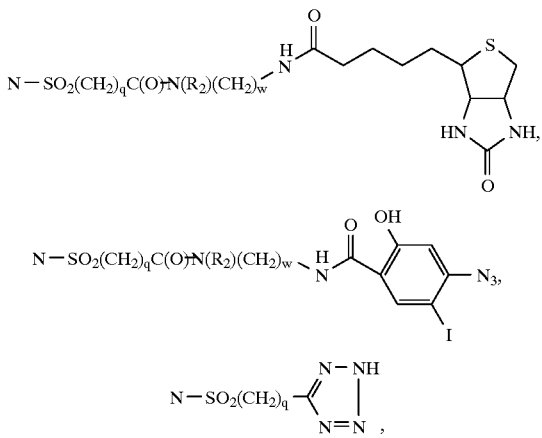

and the aryl is phenyl or pyridyl and the phenyl may be substituted by 1–2 halogen;

R$_2$ is H, or C$_1$–C$_4$ alkyl;

m is 1 or 2;

t is 0, 1, or 2;

q is 1, 2, or 3;

w is 2, 3, 4, 5, or 6;

and the pharmaceutically acceptable salts and individual diastereomers thereof.

In a subclass of the invention is the combination wherein the growth hormone secretagogue is selected from the group consisting of:

1) N-[1(R)-[(1,2-dihydro-1-methanesulfonylspiro[3H-indole-3,4'-piperidin]-1'-yl)carbonyl]-2-(1H-indol-3-yl)ethyl]-2-amino-2-methylpropanamide;

2) N-[1(R)-[(1,2-dihydro-1-methanecarbonylspiro[3H-indole-3,4'-piperidin]-1'-yl)carbonyl]-2-(1H-indol-3-yl)ethyl]-2-amino-2-methylpropanamide;

3) N-[1(R)-[(1,2-dihydro-1-benzenesulfonylspiro[3H-indole-3,4'-piperidin]-1'-yl)carbonyl]-2-(1H-indol-3-yl)ethyl]-2-amino-2-methylpropanamide;

4) N-[1(R)-[(3,4-dihydro-spiro[2H-1-benzopyran-2,4'-piperidin]-1'-yl) carbonyl]-2-(1H-indol-3-yl)ethyl]-2-amino-2-methylpropanamide;

5) N-[1(R)-[(2-acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate;

8) N-[1(R)-[(1,2-dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-dihydro-1-methanesulfonyl-5-fluorospiro[3H-indole-3,4'-piperidin]-1'-yl)carbonyl]-2-(phenylmethyloxy)ethyl]-2-amino-2-methylpropanamide;

10) N-[1(S)-[(1,2-dihydro-1-methanesulfonylspiro[3H-indole-3,4'-piperidin]-1'-yl)carbonyl]-2-(phenylmethylthio)ethyl]-2-amino-2-methylpropanamide;

11) N-[(1(R)-[(1,2-dihydro-1-methanesulfonylspiro[3H-indole-3,4'-piperidin]-1'-yl)carbonyl]-3-phenylpropyl]-2-amino-2-methylpropanamide;

12) N-[1(R)-[(1,2-dihydro-1-methanesulfonylspiro[3H-indole-3,4'-piperidin]-1'-yl)carbonyl]-3-cyclohexylpropyl]-2-amino-2-methylpropanamide;

13) N-(1(R)-[(1,2-dihydro-1-methanesulfonylspiro[3H-indole-3,4'-piperidin]-1'-yl)carbonyl]-4-phenylbutyl]-2-amino-2-methylpropanamide;

14) N-[1(R)-[(1,2-dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;

16) N-[1(R)-[(1,2-dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide; and 17) N-[1(R)-[(1,2-dihydro-1,1-dioxospiro[3H-benzothiophene-3,4'-piperidin]-1'-yl)carbonyl]-2-(phenylmethyloxy)ethyl]-2-amino-2-methylpropanamide;

or a pharmaceutically acceptable salt thereof.

Preferably, the growth hormone secretagogue used in the instant combination is N-[1(R)-[(1,2-dihydro-1-methanesulfonylspiro[3H-indole-3,4'-piperidin]-1'-yl)carbonyl]-2-(phenylmethyloxy)-ethyl]-2-amino-2-methylpropanamide, or a pharmaceutically acceptable salt thereof. Most preferably, the growth hormone secretagogue is N-[1(R)-[(1,2-dihydro-1-methanesulfonyl-spiro[3H-indole-3,4'-piperidin]- 1'-yl)carbonyl]-2-(phenylmethyloxy)-ethyl]-2-amino-2-methyl-propanamide methanesulfonate.

Further exemplifying the invention is a pharmaceutical composition which comprises any of the combinations described above and a pharmaceutically acceptable carrier. Another example of the invention is a pharmaceutical composition made by combining an estrogen receptor modulator, a growth hormone secretagogue and a pharmaceutically acceptable carrier. Further illustrating the invention is a process for making a pharmaceutical composition comprising combining an estrogen receptor modulator, a growth hormone secretagogue and a pharmaceutically acceptable carrier.

Additional illustrations of the invention are methods of treating or prevention a disease involving bone resorption which comprises administering to a patient in need of such treatment a therapeutically effective amount of any of the combinations or any of the pharmaceutical compositions described above. Preferably, the disease is osteoporosis and preferably, the patient is a human.

DESCRIPTION OF THE INVENTION

The present invention is concerned with the combination of an estrogen receptor modulator and a growth hormone secretagogue for the treatment and the prevention of disturbances of calcium and phosphate metabolism, in particular, the treatment and prevention of diseases involving bone resorption, especially, osteoporosis, Paget's disease, malignant hypercalcemia, and metastatic bone disease. This particular combination produces unexpected results in the treatment and the prevention of such clinical disturbances. Thus, it is an object of the instant invention to describe the combination of the two drugs in the treatment and prevention of diseases involving bone resorption, especially, osteoporosis. In addition, it is an object of the instant invention to describe the preferred compounds from each type of compounds which are used in the instant combination. It is a still further object of this invention to describe compositions containing each of the compounds for use in the treatment of osteoporosis. Further objects will become apparent from a reading of the following description.

The instant combination for the treatment and prevention of diseases involving bone resorption, especially osteoporosis in elderly patients, contains as a first element a growth hormone secretagogue.

Representative growth hormone secretagoues are disclosed in U.S. Pat. No. 5,206,235 is as follows:

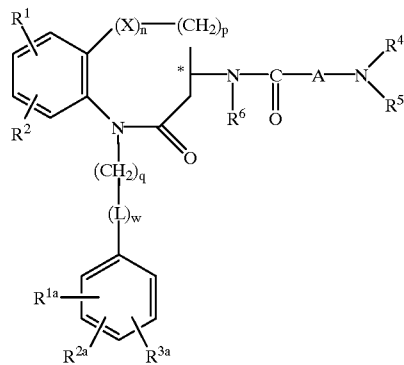

wherein the various substituents are as defined in U.S. Pat. No. 5,206,235.

Preferred growth hormone secretagogues for use in the present invention identified therein include:

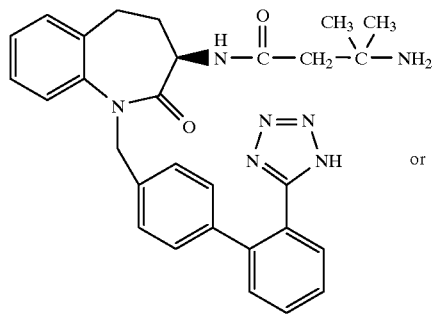

or

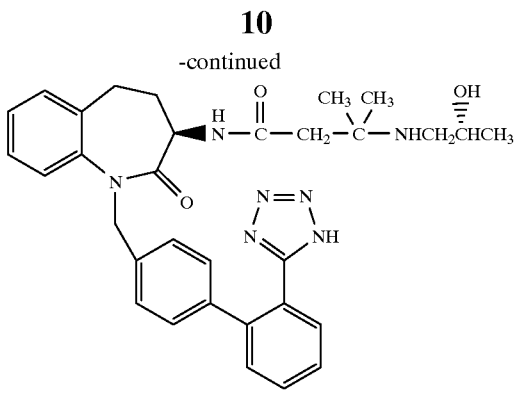

Representative growth hormone secretagoues are disclosed in U.S. Pat. No. 5,283,241 and PCT Patent Publication No. 94/05634 as benzolactam compounds of the following structural formula:

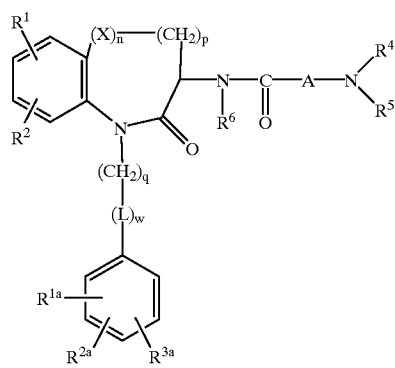

wherein the various substituents are as defined in U.S. Pat. No. 5,283,241 and PCT Patent Publication No. 94/05634.

Preferred growth hormone secretagogues for use in the present invention identified therein include:

2-amino-2-methyl-N-[2,3,4,5-tetrahydro-1-[[2'-[[[(methylamino)-carbonyl]amino]methyl][1,1'-biphenyl]-4-yl]methyl]-2-oxo-1H-benzazepin-3(R)-yl]propanamide and pharmaceutically acceptable salts thereof, in particular, the hydrochloride salt thereof.

Additional representative growth hormone secretagoues are disclosed in U.S. Pat. No. 5,536,716 as Spiro compounds of the following structural Formulas I and II:

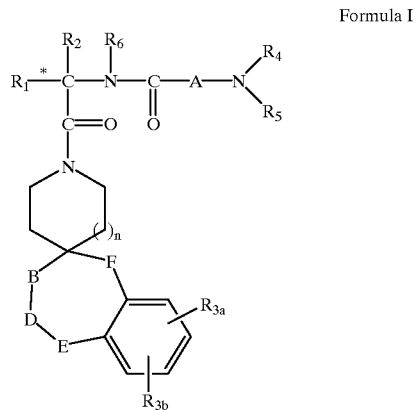

Formula I

Formula II

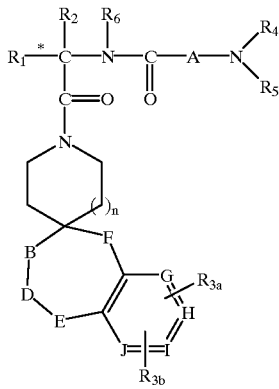

wherein the various substituents are as defined in U.S. Pat. No. 5,636,716.

Preferred growth hormone secretagogues for use in the present invention include:

N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide; and N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate.

Especially preferred growth hormone secretagogues for use in the present invention specifically include:

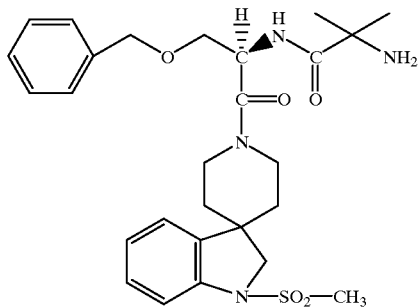

and pharmaceutically acceptable salts thereof; and

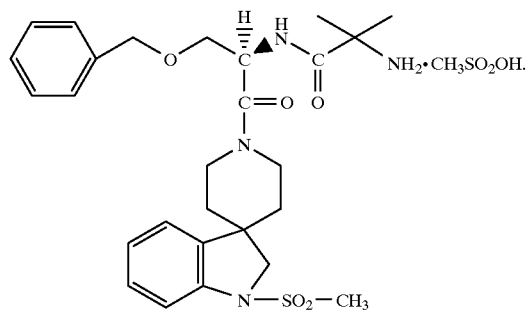

Additional representative growth hormone secretagoues are disclosed in U.S. Pat. No. 5,492,916 as being compounds of the structural formula:

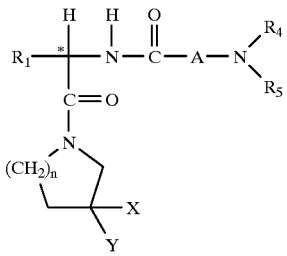

wherein the various substituents are as defined in U.S. Pat. No. 5,492,916.

Preferred growth hormone secretagogues for use in the present invention identified therein include:

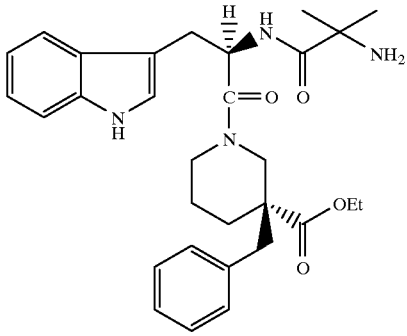

or a pharmaceutically acceptable salt thereof, especially the hydrochloride salt.

Appropriate growth hormone secretagoues for use in the present invention are found in e.g., U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Patent No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94(11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95113069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; PCT Patent Pub. No. WO 96/05195; PCT Patent Pub. No. WO 96/15148; PCT Patent Pub. No. WO 96/22782; PCT Patent Pub. No. WO 96/22997; PCT Patent Pub. No. WO 96/24580; PCT Patent Pub. No. WO 96/24587; PCT Patent Pub. No. WO 96/35713; PCT Patent Pub. No. WO 96/38471; PCT Patent Pub. No. WO 97/00894; PCT Patent Pub. No. WO 97/06803; PCT Patent Pub. No. WO 97/07117; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995). In addition, the growth hormone releasing peptides GHRP-6 and GHRP-1 are described in U.S. Pat. No. 4,411,890 and PCT Patent Pub. No. WO 89/07110, WO 89/07111, the growth hormone releasing peptide GHRP-2 is described in PCT Patent Pub. No. WO 93/04081, and the growth hormone releasing compound hexarelin is described in J. Endocrinol Invest., 15(Suppl 4), 45 (1992). The preparation of such growth hormone secretagogues is well known in the literature. Full descriptions for the preparation of growth hormone secretagogues are found in the above references.

The identification of a compound as a "growth hormone secretagogue" and thus able to directly or indirectly stimulate or increase the endogenous release of growth hormone in an animal may be readily determined without undue experimentation by methodology well known in the art, such as the assay described by Smith, et al., Science, 260, 1640–1643 (1993) (see text of FIG. 2 therein). In a typical experiment pituitary glands are aseptically removed from 150–200 g Wistar male rats and cultures of pituitary cells are prepared according to Cheng et al. Endocrinol., 124, 2791–2798 (1989). The cells are treated with the subject compound and assayed for growth hormone secreting activity and intracellular cAMP levels as described by Chang et al. In particular, the intrinsic growth horomone secretagogue activity of a compounds which may be used in the present invention may be determined by this assay.

In the instant combination for the treatment of osteoporosis, the second element is composed of an estrogen receptor modulator or a pharmaceutically acceptable salt thereof. By the term "estrogen receptor modulator" is meant any compound, with the exception of an estrogen itself, which modulates the action of an estrogen or the activity of an estrogen receptor, including "atypical estrogen agonists", "estrogen receptor mixed agonist/antagonists", "estrogen antagonists", "estrogen mimetics", "bone selective estrogens" and "antiestrogens". "Modulation" as used herein is intended to encompass antagonism, agonism, mixed agonism/antagonism, partial antagonism and/or partial agonism, whether directly or indirectly.

Appropriate estrogen receptor modulators for use in the present invention are found in e.g., U.S. Pat. No. 3,274,213; U.S. Pat. No. 4,133,814; U.S. Pat. No. 4,230,862; U.S. Pat. No. 4,323,707; U.S. Pat. No. 4,380,635; U.S. Pat. No. 4,400,543; U.S. Pat. No. 4,418,068; U.S. Pat. No. 4,536,516; U.S. Pat. No. 5,254,594; EPO Patent Pub. No. 0,062,503; EPO Patent Pub. No. 0,054,168; EPO Patent Pub. No. 0,260,066; EPO Patent Pub. No. 0,470,310; EPO Patent Pub. No. 0,651,998-0,652,005; EPO Patent Pub. No. 0,657,162; EPO Patent Pub. No. 0,659,411-0,659,429; EPO Patent Pub. No. 0,662,325; EPO Patent Pub. No. 0,663,209; EPO Patent Pub. No. 0,664,121-0,664,126; EPO Patent Pub. No. 0,665,015; EPO Patent Pub. No. 0,668,075; EPO Patent Pub. No. 0,670,162; EPO Patent Pub. No. 0,674,903; EPO Patent Pub. No. 0,683,170; EPO Patent Pub. No. 0,703,228; EPO Patent Pub. No. 0,716,855; EPO Patent Pub. No. 0,729,951; EPO Patent Pub. No. 0,729,956; EPO Patent Pub. No. 0,731,093; EPO Patent Pub. No. 0,731,098; EPO Patent Pub. No. 0,731,100; EPO Patent Pub. No. 0,733,620; EPO Patent Pub. No. 0,747,054; German Patent Pub. No. DE 2,329,201; Japan Patent Pub. No. 5,032,579; PCT Patent Pub. No. 96/09039; PCT Patent Pub. No. 96/09040; PCT Patent Pub. No. 96/09041; PCT Patent Pub. No. 96/09045; PCT Patent Pub. No. 96/09050; PCT Patent Pub. No. 96/09051; PCT Patent Pub. No. 96/09052; PCT Patent Pub. No. 96/21441; PCT Patent Pub. No. 96/22771; PCT Patent Pub. No. 96/26727; PCT Patent Pub. No. 96/26935; PCT Patent Pub. No. 96/32937; PCT Patent Pub. No. 96/39833; and Jones, et al., J. Med. Chem., 27 1057–1066 (1984).

The preparation of such estrogen receptor modulators is well known in the literature. Full descriptions for the preparation of estrogen receptor modulators are found in the above references. The utility of a compound as an estrogen receptor modulator may be demonstrated by the methodology known in the art, such as the tests and assays described in the above references.

Preferred estrogen receptor modulator compounds for use in the combinations and methods of the instant invention include: raloxifene, BE-25327, CP-336156, clometherone, delmadinone, droloxifene, idoxifene, nafoxidine, nitromifene, ormeloxifene (centchroman), tamoxifene, toremifene, trioxifene and ([2-(4-hydroxyphenyl)-6-hydroxynaphthalen-1-yl][4-[2-(1-piperidinyl)-ethoxy]phenyl]methane.

More preferred estrogen receptor modulator compounds include benzothiophenes which are described in detail in U.S. Pat. No. 4,133,814, U.S. Pat. No. 4,418,068 and Jones, et al., J. Med. Chem., 27 1057–1066 (1984).

The most preferred estrogen receptor modulator for use in the present invention is raloxifene or its pyrrolidinyl analog. Raloxifene and its preparation are described in U.S. Pat. No. 4,418,068. Raloxifene has been identified as the compound [6-hydroxy-2-(4-hydroxyphenyl)-benzo[b]thien-3-yl][4-[2-(1-piperidinyl)ethoxy]-phenyl]methanone (keoxifene, LY-139481) with the structure:

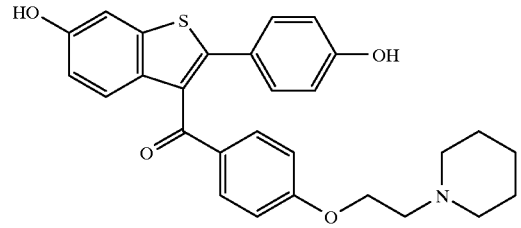

The instant combination of an estrogen receptor modulator and a growth hormone secretagogue is useful in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions.

These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency.

Combined therapy to inhibit bone resorption, prevent osteoporosis and enhance the healing of bone fractures may be illustrated by the combination of this invention of estrogen receptor modulator and growth hormone secretagogues.

The combination of an estrogen receptor modulator provides an unexpected effect in the treatment and prevention of diseases involving bone resorption when used in combination with a growth hormone secretagogue. While not being bound to any particular theory of operation, that is, an enhanced effect at reducing and reversing the rate of bone loss that occurs during the aging process, the process known as osteoporosis, is observed with the combination of drugs than would be expected from either drug alone. In particular, combination therapy of a growth hormone secretagogue and an estrogen receptor modulator increase bone mass. This increase in bone mass is possibly a result of increased bone turnover or bone formation produced by elevated growth hormone/IGF-1 levels resulting from the growth hormone secretagogue and decreased bone resorption produced by the estrogen receptor modulator. In mammals, bone formation and bone resorption generally respond to physiological stimuli and therapeutic intervention by changing in the same direction in a relationship referred to as "coupling". Treatment with an estrogen receptor modulator alone is known to decrease bone turnover by decreasing bone resorption with a concomitant ("coupled") reduction in bone formation surface. In accordance with the present invention, it is possible to promote a positive bone balance by uncoupling bone formation and bone resorption by using a combined therapeutic regime. Such uncoupling of bone formation and bone resorption would not have been predicted based on the disclosures in the art.

The instant combination of an estrogen receptor modulator and a growth hormone secretagogue is further useful in the therapeutic or prophylactic treatment of cardiovascular disorders and diseases, including cardiac protection, variant angina, enertional angina, unstable angina, ishcemia-reperfusion injury to the myocardium, arrhythminas, cerebral vascular disorders (e.g. cerebral vasospasms due to arterial rupture, stroke and migraine), renal disorders, hypertension, congestive heart failure and reduction in lipid levels.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Subacetate, Succinate, Sulfate, Sulfonate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "bone resorption," as used herein, refers to the process by which osteoclasts degrade bone.

In the above structural formulas and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, ethinyl, isopropyl, butyl, sec-butyl, tertiary butyl, pentyl, isopentyl, hexyl, isohexyl, allyl, propenyl, butenyl, butadienyl and the like. The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propinyloxy, isobutenyloxy, 2-hexenyloxy, and the like. The term "halogen" is intended to include the halogen atom fluorine, chlorine, bromine and iodine. The term "aryl" is intended to include phenyl and naphthyl and aromatic residues of 5- and 6-membered rings with 1 to 3 heteroatoms or fused 5 or 6 membered bicyclic rings with 1 to 3 heteroatoms of nitrogen, sulfur or oxygen. Examples of such heterocyclic aromatic rings are pyridine, thiophene, benzothiophene, tetrazole, indole, N-methylindole, dihydroindole, indazole, N-formylindole, benzimidazole, thiazole, furan, pyrimidine, and thiadiazole.

Certain of the above defined terms may occur more than once in the above formula and upon such occurrence each term shall be defined independently of the other.

The present invention is further directed to a method for the manufacture of a medicament for the treatment or prevention of osteoporosis which comprises an estrogen receptor modulator and a growth hormone secretagogue.

In the combination of the present invention the estrogen receptor modulator or the growth hormone secretagogue may be administered separately or in conjunction. In addition, the administration of one element may be prior to, concurrent to, or subsequent to the administration of the other agent.

The elements of the combination of the present invention may be administered by oral, parenteral (e.g., intramuscular, intraperitoneal, intravenous or subcutaneous injection, or implant), nasal, vaginal, rectal, sublingual, or topical (e.g., ocular eyedrop) routes of administration and may be formulated, alone or together, in suitable dosage unit formulations containing conventional non-toxic pharmaceutically acceptable carriers, adjuvants and vehicles appropriate for each route of administration.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient suitable for oral administration may be in the form of discrete units such as hard or soft capsules, tablets, troches or lozenges, each containing a predetermined amount of the active ingredient; in the form of a dispersible powder or granules; in the form of a solution or a suspension in an aqueous liquid or non-aqueous liquid; in the form of syrups or elixirs; or in the form of an oil-in-water emulsion or a water-in-oil emulsion. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Solid dosage forms for oral administration include capsules, tablets, pills, powders and granules. In such solid dosage forms, the active compounds are admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents.

Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintergrating agents such as corn starch, or alginic acid; (3) binding agents such as starch, gelatin or acacia; and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl disearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example calcium carbonate, calcium phosphate or kaolin. They may also be in the form of soft gelatin capsules wherein the active ingredient is mixed with water or an oil medium, for example peanut oil, liquid paraffin, or olive oil.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Aqueous suspensions normally contain the active materials in admixture with excipients suitable for the manufacture of aqueous suspensions. Such excipients may be 1) suspending agents such as sodium carboxymethylcellulose, methylcellulose, hydroxypropylmethylcellulose, sodium alginate, polyvinyl-pyrrolidone, gum tragacanth and gum acacia;

(2) dispersing or wetting agents which may be
   (a) a naturally-occurring phosphatide such as lecithin,
   (b) a condensation product of an alkylene oxide with a fatty acid, for example, polyoxyethylene sterate,
   (c) a condensation product of ethylene oxide with a long chain aliphatic alcohol, for example, heptadecaethyleneoxycetanol,
   (d) a condensation product of ethylene oxide with a partial ester derived from a fatty acid and a hexitol such as polyoxyethylene sorbitol monooleate, or
   (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an anti-oxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension or solution. The suspension may be formulated according to known methods using those suitable dispersing or wetting agents and suspending agents which have been mentioned above. The sterile injectable preparation may also be a sterile injectable solution or suspension in a non-toxic paternterallyacceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Preparations according to this invention for parenteral administration include sterile aqueous or non-aqueous solutions, suspension, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. The combination of this invention may also be administered in the form of suppositories for rectal administration. This composition can be prepared by mixing the drug with a suitable non-irritating excipient which is solid at ordinary temperatures but liquid at the rectal temperature and will therefore melt in the rectum to release the drug. Such materials are cocoa butter and polyethylene gylcols. Compositions for nasal or sublingual administration are also prepared with standard excipients well known in the art.

For topical administration the combination of this invention may be formulated in liquid or semi-liquid preparations such as liniments, lotions, applications; oil-in-water or water-in-oil emulsions such as creams, ointments, jellies or pastes, including tooth-pastes; or solutions or suspensions such as drops, and the like.

The pharmaceutical composition and method of the present invention may further comprise other therapeutically active compounds usually applied in the treatment of the above mentioned pathological conditions, for instance vitamin $D_2$ and $D_3$ and hydroxylated derivatives, e.g. 1α-hydroxy-vitamin $D_3$, 1α-hydroxy-vitamin $D_2$, 1α-25-dihydroxy-vitamin $D_3$, 1α-25-dihydroxy-vitamin $D_2$, dehydroepiandrosterone, calcitonin (human, porcine or salmon), mitramycin, sodium fluoride, calcium supplements such as calcium carbonate, estrogens, and non-steroid anti-inflammatory drugs, such as acetylsalicyclic acid, indomethacin, naprosyn, and timegadine, and bisphosphonates. The use of bisphosphonates for utility in bone diseases has been reviewed, for example, by Hamdy, N.A.T., Role of Bisphosphonates in Metabolic Bone Diseases, *Trends in Endocrinol. Metab.*, 4, 19–25 (1993). Bisphosphonates useful for treating bone diseases, such as osteoporosis, include alendronate, tiludronate, dimethyl-APD, risedronate, etidronate, YM-175, clodronate, pamidronate, and BM-210995, a preferred bisphosphonate being alendronate, and especially alendronate sodium. A preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

The dosage of the active ingredients in the compositions of this invention may be varied. However, it is necessary that the amount of the active ingredient be such that a suitable dosage form is obtained. The selected dosage depends upon the desired therapeutic effect, on the route of administration and on the duration of the treatment. Dosage ranges in the combination for the growth hormone secretogogue and the estrogen receptor modulator are one tenth to one times the clinically effective ranges required to elevate growth hormone and reduce bone resorption respectively when the compounds are used singly. Generally, dosage levels of the estrogen receptor modulator of between about 0.01 mg per kg of body weight per day (mg/kg/day) to about 1000 mg/kg/day, preferably 0.01 to 100 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of each of the active ingredients for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Dosage levels of the growth hormone secretatogogue of between about 0.0001 to 50 mg/kg of body weight daily, preferably about 0.001 to about 25 mg/kg per day, and more preferably about 0.01 to about 10 mg/kg per day are administered to a patient to obtain effective treatment or prevention of osteoporosis.

An especially preferred combination is that wherein the growth hormone secretagoguge is N-[1(R)-[(1,2-dihydro-1-methanesulfonylspiro[3H-indole-3,4'-piperidin]-1'-yl) carbonyl]-2-(phenylmethyloxy)ethyl]-2-amino-2-methylpropanamide, in particular the methanesulfonate salt thereof, and the estrogen receptor modulator is raloxifene. In this especially preferred combination dosage levels of each component are as noted above, however, it is even more preferred that the estrogen receptor modulator raloxifene may be administered at a dosage rate of about 0.1 to about 10 mg/kg/day, especially about 0.5 to about 5.0 mg/kg/day, and more particularly about 1 to about 5 mg/kg/day, and that N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate be administered at a dosage level of about 0.001 to about 20 mg/kg/day, especially about 0.005 to about 10 mg/kg/day, and more particularly about 0.01 to about 5 mg/kg/day.

The instant combination may also be administered on an intermittent basis. For the treatment or prophylaxis of diseases involving bone resorption a typical primary oral dose of estrogen receptor modulator which lies within the range of from about 0.001 mg to 100 mg per kg body weight and a dose of growth hormone secretatogoue of between 0.0001 to 25 mg per kg of body weight may be administered and then, if necessary a sustaining dose of one element or both elements approximately equal to half of the primary dose may be administered at weekly, semiweekly, semimonthly, monthly, bimonthly, quarterly, semiannual, annual or biannual intervals. Similarly, the estrogen receptor modulator and the growth hormone secretagogue may be administered in a cyclical manner and it is not necessary that each component be administered concomitantly.

The compounds which are employed in the combination of the present invention are prepared by the references cited above.

The following examples are provided for the purpose of further illustration only and are not intended to be limitations on the spirit or scope of the present invention.

The test procedures employed to measure the bone resorption inhibiting activity of the compounds of the present invention are described below.

EXAMPLE 1
Bone Resorption-Pit Assay

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a six mm cylinder of bovine femur diaphysis were cut with a low speed diamond saw (Isomet, Beuler, Ltd., Lake Bluff, Ill.). Bone slices were pooled, placed in a 10% ethanol solution and refrigerated until further use.

Prior to experimentation, bone slices were ultrasonicated twice, 20 minutes each in $H_2O$. Cleaned slices were placed in 96 well plates such that two control lanes and one lane for each drug dosage are available. Each lane represents either triplicate or quadruplicate cultures. The bone slices in 96 well plates were sterilized by UV irradiation. Prior to incubation with osteoclasts, the bone slices were hydrated by the addition of 0.1 ml Medium 199, pH 6.9 containing 15% fetal bovine serum and 1% penicillin/streptomycin.

Osteoclasts were isolated from the long bones of 1 to 3 day old rat pups (Sprague-Dawley) by modifications of Chambers et al., (J. Cell. Science, 66:383–399). The resulting suspension (0.75 ml/bone) was gently triturated 90–120 times using a wide bore transfer pipet. The cellular population was separated from bone fragments by a cell strainer with a 100 micron nylon mesh. 100 $\mu$l of the cell suspension was placed onto each bone slice. Test compounds were then added at the desired experimental concentrations.

Bone slices exposed to osteoclasts for 20–24 hrs were processed for staining. Tissue culture media was removed from each bone slice. Each well was washed with 200 $\mu$l of $H_2O$, and the bone slices were then fixed for 20 minutes in 2.5% glutaraldehyde, 0.1M cacodylate, pH 7.4. After fixation, any remaining cellular debris was removed by 2 min. ultrasonication in the presence of 0.25M $NH_4OH$ followed by 2×15 min ultrasonication in $H_2O$. The bone slices were immediately stained for 6–8 min with filtered 1% toluidine blue and 1% borax.

After the bone slices have dried, resorption pits were counted in test and control slices. Resorption pits were viewed in a Microphot Fx (Nikon) fluorescence microscope using a polarizing Nikon IGS filter cube. Test dosage results were compared with controls and resulting $IC_{50}$ values were determined for each compound tested.

The appropriateness of extrapolating data from this assay to utility and use in mammalian (including human) disease states is supported by the teaching found in Sato, M., et al., *Journal of Bone and Mineral Research*, Vol. 5, No. 1, 1990. That article teaches that certain compounds have been used clinically and appear to be effective in the treatment of Paget's disease, hypercalcemia of malignancy, osteolytic lesions produced by bone metastases, and bone loss due to immobilization or sex hormone deficiency. These same compounds are then tested in the resorption pit assay described above to confirm a correlation between their known utility and positive performance in the assay.

EXAMPLE 2
Ocform Assay

Osteoblast-like cells (1.8 cells), originally derived from mouse calvaria, were plated in CORNING 24 well tissue culture plates in $\alpha$ MEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 $\mu$m nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1\times10^6$ cells/mL. 50 $\mu$L was added to each well of 1.8 cells to yield 50,000 cells/well and 1,25-dihydroxy-vitamin $D_3(D_3)$ was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS -MX phosphate. After staining, the plates were washed extensively with deionized water and air dried. The number of multinucleated, positive staining cells were counted in each well.

EXAMPLE 3
Combined Therapy with N-[1(R)-[(1,2-Dihydro-1-methanesulfonylspiro[3H-indole-3,4'-piperidin]-1'-yl)carbonyl]-3-phenylpropyl]-2-amino-2-methyl-propanamide and Raloxifene Exploratory Nine(9)-Week Bone Study in Old Female Rats The purpose of this study is to evaluate the effect of N-[1(R)-[(1,2-dihydro-1-methane-sulfonylspiro[3H-indole-3,4'-piperidin]-1'-yl)carbonyl]-3-phenylpropyl]-2-amino-2-methyl-propanamide, alone and in combination with the estrogen receptor modulator raloxifene, on the bone in old female rats. The duration of the study is 9 weeks. The frequency of dosing with N-[1(R)-[(1,2-dihydro-1-methanesulfonylspiro[3H-indole-3,4'-piperidin]-1'-yl)

carbonyl]-3-phenylpropyl]-2-amino-2-methyl-propanamide is once daily, seven days a week. The frequency of dosing with raloxifene is once daily. The route of administration of N-[1(R)-[(1,2-dihydro-1-methane-sulfonylspiro[3H-indole-3 ,4'-piperidin]-1'-yl)carbonyl]-3-phenylpropyl]-2-amino-2-methylpropanamide is orally by gavage and raloxifene is orally by gavage. The control article is distilled water and the carrier is distilled water. The dosing volume of N-[1(R)-[(1,2-dihydro-1-methane-sulfonylspiro[3H-indole-3,4'-piperidin]-1'-yl)carbonyl]-3-phenylpropyl]-2-amino-2-methylpropanamide is 5 ml/kg, and the dosing volume of raloxifene is 5 ml/kg. The test system is the female rat of a strain Sprague-Dawley Crl:CD® (SD) BR, which were of an approximate age at the start of the study of greater than 6 months, and which are of an approximate weight at the start of the study of 250–350 g. There should be no contaminants in the feed and water that are known to interfere with the purpose and conduct of this study. There should be no contaminants in the bedding that are known to interfere with the purpose and conduct of this study. The rats are housed in individual stainless steel wire cages.

| | Number of Animals | |
|---|---|---|
| Dosage levels | Males | Females |
| Control 1 | 0 | 7 |
| Control 2 (Distilled water) | 0 | 8 |
| N-[1(R)-[(1,2-Dihydro-1-methane-sulfonyl-spiro[3H-indole-3,4'-piperidin]-1'-yl)-carbonyl]-3-phenylpropyl]-2-amino-2-methyl-propanamide [50 mg/kg/day] | 0 | 11 |
| Raloxifene [10 mg/kg/day] | 0 | 10 |
| N-[1(R)-[(1,2-Dihydro-1-methane-sulfonyl-spiro[3H-indole-3,4'-piperidin]-1'-yl)-carbonyl]-3-phenylpropyl]-2-amino-2-methyl-propanamide + Raloxifene [50 mg/kg/day + 10 mg/kg/day] | | 12 |

HORMONE ANALYSIS

Drug Day 1: Blood sampling (approximately 1.5 ml) is from orbital sinus on non-fasted rats, all groups, for measurements of GH; bleeding is done 15 minutes post dosing in control groups and groups receiving N-[1(R)-[(1,2-dihydro-1-methane-sulfonylspiro[3H-indole-3,4'-piperidin]-1'-yl)carbonyl]-3-phenylpropyl]-2-amino-2-methylpropanamide alone or in combination.

Drug Weeks 2*, 9:

Blood sampling (approximately 1.5 ml) is from orbital sinus on non-fasted rats, all groups except control group 1, for measurement of GH; bleeding is done 15 minutes post dosing in control group 2 and groups receiving N-[1(R)-[(1, 2-dihydro-1-methane-sulfonylspiro[3H-indole-3,4'-piperidin]-1'-yl)carbonyl]-3-phenylpropyl]-2-amino-2-methylpropanamide alone or in combination;

Blood sampling (volume: as much as possible) is from cava at necropsy, on non-fasted rats, all groups for measurement of IGF-1. (* for control group 1, only)

Growth Hormone Levels (Day 1) are measured for each treatment group.

BONE ANALYSIS

All rats received bone labelling agents (oxytetracycline and calcein): 9 days (oxytetracycline) and 2 days (calcein), before necropsy. Oxytetracycline is injected subcutaneously twice (2 injections approximately 5 hours apart) at a dose level of 25 mg/kg, and calcein is injected intraperitonally at a dose level of 15 mg/kg.

Tibiae are processed through increasing concentrations of ethanol followed by methyl methacrylate embedding, using an automated Hypercenter XP tissue processor (Shandon-Lipshaw, Pittsburgh, Pa.). Five micron thick sections are cut using a Reichert-Jung Polycut-S microtome and stained with Bioquant Image Analysis System (R&M Biometrics, Nashville, Tenn.). Measured and calculated parameters included; cancellous bone volume expressed as a percent of tissue volume (VB/TV, %), osteoblast surface expressed as a percent of trabecular bone surface (ObS/BS, %), osteoclastic erosion surface expressed as a percent of trabecular bone surface (ES/BS, %), the number of osteoclasts per unit bone surface (NOcIBS, #mm), trabecular thickness (TbTh, $\mu$m), trabecular separation (TbSp, $\mu$m), and trabecular number (TbN, #/mm). All measurements are made in the metaphyseal secondary spongiosa 1 mm below the epiphyseal growth plate. Length of the tibia is measured and diaphyseal cortical cross sections are cut using a Buehler ISOMET saw 1 cm proximal to the tibiofibular junction. Results are expressed as mean SEM. Statistical analysis is performed using the package STATVIEW for Macintosh (Abacus Concepts, Berkeley, Calif.). Differences between treatment groups are tested by one-way analysis of variance and Fisher PLSD (protected least significant difference). A value of $p<0.05$ is considered significant.

EXAMPLE 4

Combined Therapy with N-[1(R)-[(1,2-Dihydro-1-methanesulfonylspiro[3H-indole-3,4'-piperidin]-1'-yl) carbonyl]-2-(phenylmethyloxy)ethyl]-2-amino-2-methylpropanamide and Raloxifene: Nine (9) Week Bone Study in Female Dogs The purpose of this study is to evaluate the combined effects of nine weeks treatment with the growth hormone secretagogue ("GHS"), N-[1(R)-[(1,2-dihydro-1-methanesulfonylspiro[3H-indole-3,4'-piperidin]-1'-yl) carbonyl]-2-(phenylmethyloxy)ethyl]-2-amino-2-methylpropanamide methanesulfonate, and the estrogen receptor modulator, raloxifene, on bone mineral density and bone formation in dogs.

One year old female (9.1–13 kg) dogs are assigned four per dose group and treated for nine weeks with either vehicle, or 1.25 mg/kg/day GHS+0.5 mg/kg/day estrogen receptor modulator, 2.5 mg/kg/day GHS+1.0 mg/kg/day estrogen receptor modulator, or 5.0 mg/kg/day GHS+2.0 mg/kg/day estrogen receptor modulator. To identify formation surfaces dogs receive fluorochrome bone labels prior to necropsy by i.v. administration of oxytetracycline (15 mg/kg i.v.) and calcein (15 mg/kg i.v.) with a 14 day interval between the administration of the two labels. At necropsy, the fourth and fifth lumbar vertebrae and right tibiae are dissected free of muscle and other connective tissue and fixed in cold 70% ethanol (4° C.). Spinous and transverse processes of vertebra L5 are removed, the vertebral body is submerged in two inches of water, and bone mineral content is measured using dual energy x-ray absorptiometry (QDR 4500A, HOLOGIC, Waltham Mass.). The L5 vertebral body is then cut in cross-section and a central sagittal piece of the proximal portion is cut using a high speed Dremmel tool. The vertebral cross and sagittal sections are processed and embedded in methylmethacrylate without prior decalcification using a Hypercenter XP tissue processor (Shandon, Pittsburgh, Pa.). Sagittal and cross-sections of 6–10 $\mu$m thickness are cut using a Polycut S microtome (Leica, Deerfield, Ill.).

All morphometric measurements are performed using the Bone Morphometry software (Bioquant System IV, Nashville, Tenn.), a computer with a digitizing board and a microscope equipped with visible and UV light sources. For each specimen, the following cancellous bone parameters are measured in a mean tissue area of 4.6 mm² located in the metaphyseal region of the vertebra beginning 2 mm inferior to the growth plate. Using bright field illumination, the following variables of cancellous bone structure: bone volume/tissue volume (BV/TV, %), trabecular number (Tb. N, #/mm), trabecular thickness (TbTh., μm), trabecular separation (Tb Sp., μm) are directly measured or calculated from primary measurements of tissue area, trabecular bone area, trabecular bone perimeter and boundary length, using Masson's trichrome stained sections. Osteoid surface (OS/BS, %) or the unmineralized matrix is also measured on Masson's trichrome stained sections in the same area and expressed as a percent of the trabecular bone surface. Osteoid thickness (O.Th, μm) is calculated as the product of osteoid width and the correction factor π/4. Mineralization lag time (Mlt, days) is calculated as O.Th/Aj.AR. Adjusted apposition rate (Aj.AR, μm/d) or effective apposition rate is calculated as the product of MAR*(MS/OS). The vertebral anterior (ventral) cortical width is also directly measured from stained mid-vertebral cross-sections.

Dynamic labeled parameters are assessed in the same area of 10 μm thick sections viewed under epifluorescence by measuring the length of the oxytetracycline and calcein labels on trabecular bone surface and the interlabel distance. The mineralizing surface (MS/BS, %) is calculated as one-half the length of single labels plus the length of double labels expressed as a percent of bone surface. The mineral appositional rate (MAR, μm/day) is calculated as the mean distance between the first and second label at equidistant points divided by the labeling interval (14 days) and then multiplied by the correction factor (π/4) to account for the obliquity of the sectioning plane. Surface based bone formation rate (BFR/BS) is calculated as the product of MS*MAR and expressed per year.

Statistical analysis of histomorphometric data is done using the statistical package Statview™ (Macintosh). Differences between treatment group are tested by one-way analysis of variance. If significant differences are indicated by ANOVA, comparison between groups means are tested by the Fisher Protected Least Significant Difference test (PLSD, p<0.05). Bone densitometry data are analyzed using a Statistical Trend Analysis (NOSTASOT) test to assess the effect of increasing drug doses.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A combination which comprises an estrogen receptor modulator and a growth hormone secretagogue.

2. The combination of claim 1 wherein the growth hormone secretagogue is of the Formula I or II:

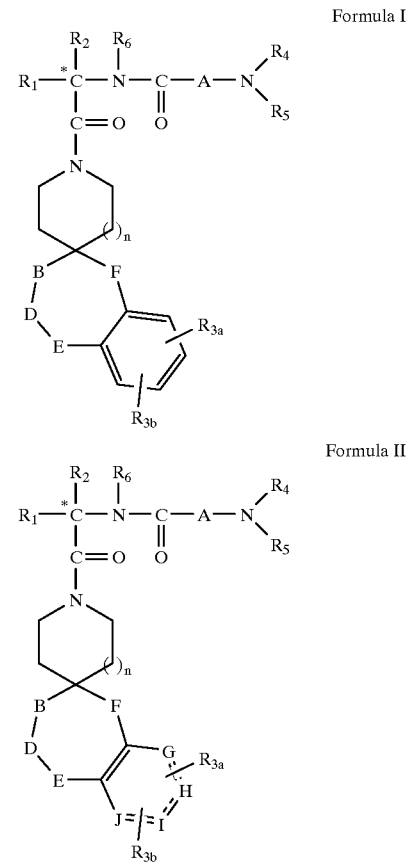

wherein:
  $R_1$ is selected from the group consisting of:
    —$C_1$–$C_{10}$ alkyl, -aryl, aryl-($C_1$–$C_6$ alkyl)—,
    $C_3$–$C_7$ cycloalkyl-($C_1$–$C_6$alkyl)-, -$C_1$–$C_5$alkyl-K-$C_1$–$C_5$ alkyl, aryl($C_0$–$C_5$alkyl)-K-($C_1$–$C_5$ alkyl)-, and
    $C_3$–$C_7$ cycloalkyl($C_0$–$C_5$ alkyl)-K-($C_1$–$C_5$ alkyl)-, wherein K is O, S(O)$_m$, N($R_2$)C(O), C(O)N($R_2$), OC(O), C(O)O, or —C$R_2$=C$R_2$—, or —C≡C—,
    and wherein the aryl groups are as defined below and the $R_2$ and alkyl groups may be further substituted by 1 to 9 halogen, S(O)m$R_{2a}$, 1 to 3 O$R_{2a}$, or C(O) O$R_{2a}$, and the aryl groups may be further substituted by phenyl, phenoxy, halophenyl, 1–3 $C_1$–$C_6$ alkyl, 1 to 3 halogen, 1 to 2—O$R_2$, methylenedioxy, —S(O)$_m$$R_2$, 1 to 2—C$F_3$, —OC$F_3$, nitro, —N($R_2$) (R2), —N($R_2$)C(O)$R_2$, —C(O)O$R_2$, —C(O)N($R_2$) ($R_2$), —SO$_2$N($R_2$)($R_2$), —N($R_2$)S(O)$_2$ aryl, and —N($R_2$)SO$_2$$R_2$;
  $R_2$ is selected from the group consisting of:
    hydrogen, $C_1$–$C_6$ alkyl, $C_3$–$C_7$ cycloalkyl, and where two $C_1$–$C_6$ alkyl groups are present on one atom, they may be optionally joined to form a $C_3$–$C_8$ cyclic ring optionally including oxygen, sulfur or N$R_{2a}$;
  $R_{2a}$ is hydrogen, or $C_1$–$C_6$ alkyl;
  $R_{3a}$ and $R_{3b}$ are independently selected from the group consisting of:
    hydrogen, halogen, —$C_1$–$C_6$ alkyl, —O$R_2$, cyano, —OC$F_3$, methylenedioxy, nitro, —S(O)$_m$R, —C$F_3$ or —C(O)O$R_2$ and when $R_{3a}$ and $R_{3b}$ are in an ortho arrangement, they may be joined to form a $C_5$ to $C_8$ aliphatic or aromatic ring optionally including 1 or 2 heteroatoms selected from oxygen, sulfur or nitrogen;

$R_4$ and $R_5$ are independently selected from the group consisting of:
hydrogen, $-C_1-C_6$ alkyl, substituted $C_1-C_6$ alkyl wherein the substituents are selected from 1 to 5 halo, 1 to 3 hydroxy, 1 to 3 $C_1-C_{10}$ alkanoyloxy, 1 to 3 $C_1-C_6$ alkoxy, phenyl, phenoxy, 2-furyl, $C_1-C_6$ alkoxycarbonyl, $-S(O)_m(C_1-C_6$ alkyl); or $R_4$ and $R_5$ can be taken together to form $-(CH_2)_rL_a(CH_2)_s-$ where $L_a$ is $-C(R_2)_2-$, $-O-$, $-S(O)_m-$, or $-N(R_2)-$, where r and s are independently 1 to 3 and $R_2$ is as defined above;

$R_6$ is hydrogen or $C_1-C_6$ alkyl;

A is:

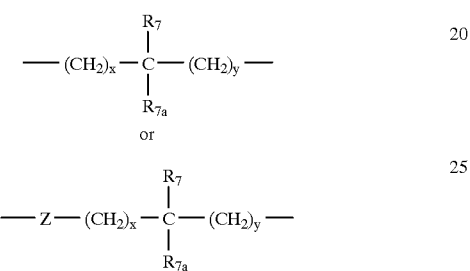

wherein x and y are independently 0–3;

Z is $N-R_2$ or O;

$R_7$ and $R_{7a}$ are independently selected from the group consisting of:
hydrogen, $-C_1-C_6$ alkyl, $-OR_2$, trifluoromethyl, phenyl, substituted $C_1-C_6$ alkyl where the substituents are selected from imidazolyl, phenyl, indolyl, p-hydroxyphenyl, $-OR_2$, 1 to 3 fluoro, $-S(O)_mR_2$, $-C(O)OR_2$, $-C_3-C_7$ cycloalkyl, $-N(R_2)(R_2)$, $-C(O)N(R_2)(R_2)$; or $R_7$ and $R_{7a}$ can independently be joined to one or both of $R_4$ and $R_5$ groups to form alkylene bridges between the terminal nitrogen and the alkyl portion of the $R_7$ or $R_{7a}$ groups, wherein the bridge contains 1 to 5 carbons atoms;

B, D, E, and F are independently selected from the group consisting of:
$-C(R_8)(R_{10})-$, $-O-$, $C=O$, $-S(O)_m-$, or $-NR_9-$, such that one or two of B, D, E, or F may be optionally absent to provide a 5, 6, or 7 membered ring; and provided that B, D, E and F can be $-C(R_8)(R_{10})-$ or $C=O$ only when one of the remaining B, D, E and F groups is simultaneously $-O-$, $-S(O)_m-$, or $-NR_9-$, or B and D, or D and E taken together may be $-N=CR_{10}-$ or $-CR_{10}=N-$, or B and D, or D and E taken together may be $-CR_8=CR_{10}-$, provided one of the other of B and E or F is simultaneously $-O-$, $-S(O)_m-$, or $-NR_9-$;

$R_8$ and $R_{10}$ are independently selected from the group consisting of:
hydrogen, $-R_2$, $-OR_2$, $(-CH_2)_q$-aryl, $-(CH_2)_{q-C(O)OR_2}$, $-(CH_2)_q-C(O)O(CH_2)_q$-aryl, or $-(CH_2)_q$-(1H-tetrazol-5-yl), where the aryl may be optionally substituted by 1 to 3 halo, 1 to 2 $C_1-C_8$ alkyl, 1 to 3-$OR_2$ or 1 to 2-$C(O)OR_2$;

$R_9$ is selected from the group consisting of:
$-R_2$, $-(CH_2)_q$-aryl, $-C(O)R_2$, $-C(O)(CH_2)_q$-aryl, $-SO_2R_2$, $-SO_2(CH_2)_q$-aryl, $-C(O)N(R_2)(R_2)$, $-C(O)N(R_2)(CH_2)_q$-aryl, $-C(O)OR_2$, 1-H-tetrazol-5-yl, $-SO_3H$, $-SO_2NHC\equiv N$, $-SO_2N(R_2)$aryl, $-SO_2N(R_2)(R_2)$, and wherein the $(CH_2)_q$ may be optionally substituted by 1 to 2 $C_1-C_4$ alkyl, and the $R_2$ and aryl may be optionally further substituted by 1 to 3-$OR_{2a}$, $-O(CH_2)_q$ aryl, 1 to 2-$C(O)OR_{2a}$, 1 to 2-$C(O)O(CH_2)_q$ aryl, 1 to 2-$C(O)N(R_{2a})(R_{2a})$, 1 to 2-$C(O)N(R_{2a})(CH_2)_q$ aryl, 1 to 5 halogen, 1 to 3 $C_1-C_4$ alkyl, 1,2,4-triazolyl, 1-H-tetrazol-5-yl, $-C(O)NHSO_2R_{2a}$, $-S(O)_mR_{2a}$, $-C(O)NHSO_2(CH_2)_q$-aryl, $-SO_2NHC\equiv N$, $-SO_2NHC(O)R_{2a}$, $-SO_2NHC(O)(CH_2)_q$aryl, $-N(R_2)C(O)N(R_{2a})(R_{2a})$, $-N(R_{2a})C(O)N(R_{2a})(CH_2)_q$-aryl, $-N(R_{2a})(R_{2a})$, $-N(R_{2a})C(O)R_{2a}$, $-N(R_{2a})C(O)(CH_2)_q$ aryl, $-OC(O)N(R_{2a})(R_{2a})$, $-OC(O)N(R_{2a})(CH_2)_q$ aryl, $-SO_2(CH_2)_qCONH-(CH_2)wNHC(O)R_{11}$, wherein w is 2–6 and $R_{11}$ may be biotin, aryl, or aryl substituted by 1 or 2 $OR_2$, 1–2 halogen, azido or nitro;

m is 0, 1 or 2;

n is 1, or 2;

q may optionally be 0, 1, 2, 3, or 4; and

G, H, I and J are carbon, nitrogen, sulfur or oxygen atoms, such that at least one is a heteroatom and one of G, H, I or J may be optionally missing to afford a 5 or 6 membered heterocyclic aromatic ring;

and pharmaceutically acceptable salts and individual diastereomers thereof.

3. The combination of claim 1 wherein the growth hormone secretagogue is of the Formula V:

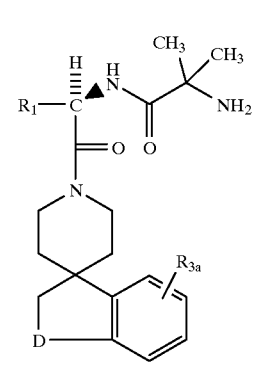

wherein:

$R_1$ is selected from the group consisting of:

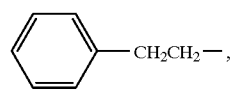 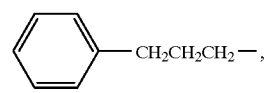

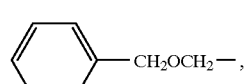 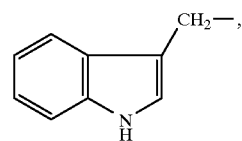

-continued

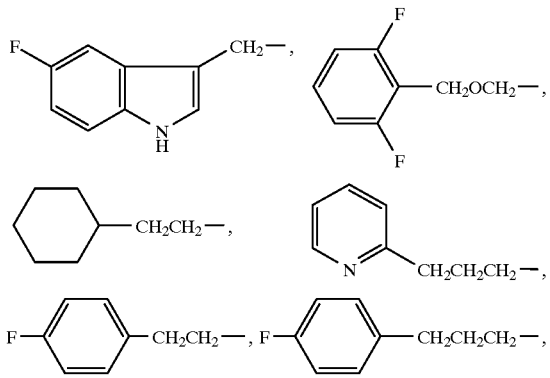

$R_{3a}$ is H, or fluoro;
D is selected from the group consisting of:
—O—, —S—, —S(O)$_m$—, N(R$_2$), NSO$_2$(R$_2$), NSO$_2$(CH$_2$)taryl, NC(O)(R$_2$), NSO$_2$(CH$_2$)$_q$OH, NSO$_2$(CH$_2$)$_q$COOR$_2$, NSO$_2$(CH$_2$)$_q$C(O)—N(R$_2$)(R$_2$), N—SO$_2$(CH$_2$)$_q$C(O)—N(R$_2$)(CH$_2$)wOH,

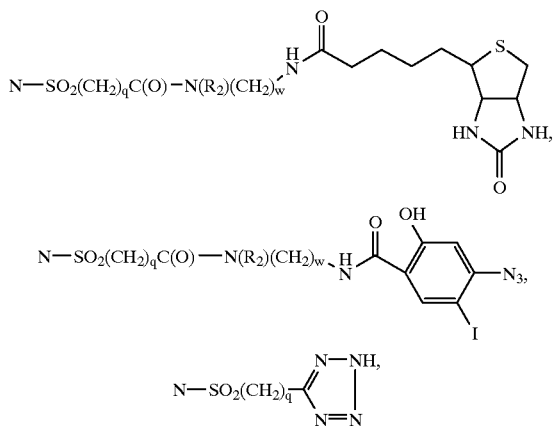

and the aryl is phenyl or pyridyl and the phenyl may be substituted by 1–2 halogen;
R$_2$ is H, or C$_1$–C$_4$ alkyl;
m is 1 or 2;
t is 0, 1, or 2;
q is 1, 2, or 3;
w is 2, 3, 4, 5, or 6;
and the pharmaceutically acceptable salts and individual diastereomers thereof.

4. The combination of claim 1 wherein the growth hormone secretagogue is selected from the group consisting of:
1) N-[1(R)-[(1,2-dihydro-1-methanesulfonylspiro[3H-indole-3,4'-piperidin]-1'-yl)carbonyl]-2-(1H-indol-3-yl)ethyl]-2-amino-2-methylpropanamide;
2) N-[1(R)-[(1,2-dihydro-1-methanecarbonylspiro[3H-indole-3,4'-piperidin]-1'-yl)carbonyl]-2-(1H-indol-3-yl)ethyl]-2-amino-2-methylpropanamide;
3) N-[1(R)-[(1,2-dihydro-1-benzenesulfonylspiro[3H-indole-3,4'-piperidin]-1'-yl)carbonyl]-2-(1H-indol-3-yl)ethyl]-2-amino-2-methylpropanamide;
4) N-[1(R)-[(3,4-dihydro-spiro[2H-1-benzopyran-2,4'-piperidin]-1'-yl) carbonyl]-2-(1H-indol-3-yl)ethyl]-2-amino-2-methylpropanamide;
5) N-[1(R)-[(2-acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-dihydro-1-methanesulfonyl-5-fluorospiro[3H-indole-3,4'-piperidin]-1'-yl)carbonyl]-2-(phenylmethyloxy)ethyl]-2-amino-2-methylpropanamide;
10) N-[1(S)-[(1,2-dihydro-1-methanesulfonylspiro[3H-indole-3,4'-piperidin]-1'-yl)carbonyl]-2-(phenylmethylthio)ethyl]-2-amino-2-methylpropanamide;
11) N-[1(R)-[(1,2-dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide; and
17) N-[1(R)-[(1,2-dihydro-1,1-dioxospiro[3H-benzothiophene-3,4'-piperidin]-1'-yl)carbonyl]-2-(phenylmethyloxy)ethyl]-2-amino-2-methylpropanamide;
or a pharmaceutically acceptable salt thereof.

5. The combination of claim 1 wherein the growth hormone secretagogue is selected from the group consisting of:
N-[1(R)-[(1,2-dihydro-1-methanesulfonyl-spiro[3H-indole-3,4'-piperi din]-1'-yl)carbonyl]-2-(phenylmethyloxy)-ethyl]-2-amino-2-methylpropanamide, or a pharmaceutically acceptable salt thereof.

6. The combination of claim 1 wherein the growth hormone secretagogue is N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide methanesulfonate.

7. The combination of claim 1 wherein the estrogen receptor modulator is selected from the group consisting of: raloxifene, BE-25327, CP-336156, clometherone, delmadinone, droloxifene, idoxifene, nafoxidine, nitromifene, ormeloxifene (centchroman), tamoxifene, toremifene, trioxifene and ([2-(4-hydroxyphenyl)-6-hydroxynaphthalen-1-yl][4-[2-(1-piperidinyl)ethoxy]phenyl]methane or a pharmaceutically acceptable salt thereof.

8. The combination of claim 2 wherein the estrogen receptor modulator is selected from the group consisting of: raloxifene, BE-25327, CP-336156, clometherone, delmadinone, droloxifene, idoxifene, nafoxidine, nitromifene, ormeloxifene (centchroman), tamoxifene, toremifene, trioxifene and ([2-(4-hydroxyphenyl)-6-hydroxynaphthalen-1-yl][4-[2-(1-piperidinyl)ethoxy]phenyl]methane or a pharmaceutically acceptable salt thereof.

9. The combination of claim 3 wherein the estrogen receptor modulator is selected from the group consisting of: raloxifene, BE-25327, CP-336156, clometherone, delmadinone, droloxifene, idoxifene, nafoxidine, nitromifene, ormeloxifene (centchroman), tamoxifene, toremifene, trioxifene and ([2-(4-hydroxyphenyl)-6-hydroxynaphthalen-1-yl][4-[2-(1-piperidinyl)ethoxy]phenyl]methane or a pharmaceutically acceptable salt thereof.

10. The combination of claim 4 wherein the estrogen receptor modulator is selected from the group consisting of: raloxifene, BE-25327, CP-336156, clometherone, delmadinone, droloxifene, idoxifene, nafoxidine, nitromifene, ormeloxifene (centchroman), tamoxifene, toremifene, trioxifene and ([2-(4-hydroxyphenyl)-6-hydroxynaphthalen-1-yl][4-[2-(1-piperidinyl)ethoxy]phenyl]methane or a pharmaceutically acceptable salt thereof.

11. The combination of claim 4 wherein the estrogen receptor modulator is selected from the group consisting of: raloxifene, or a pharmaceutically acceptable salt thereof.

12. The combination of claim 5 wherein the estrogen receptor modulator is selected from the group consisting of: raloxifene, or a pharmaceutically acceptable salt thereof.

13. A pharmaceutical composition which comprises the combination of claim 1 and a pharmaceutically acceptable carrier.

14. A pharmaceutical composition made by combining an estrogen receptor modulator, a growth hormone secretagogue and a pharmaceutically acceptable carrier.

15. A process for making a pharmaceutical composition comprising combining an estrogen receptor modulator, a growth hormone secretagogue and a pharmaceutically acceptable carrier.

16. A method of treating or preventing a disease involving bone resorption which comprises administering to a patient in need of such treatment a therapeutically effective amount of the combination of claim 1.

17. The method of claim 16 wherein the disease is osteoporosis.

18. The method of claim 17 wherein the patient is a human.

19. A method of treating or preventing a disease involving bone resorption which comprises administering to a patient in need of such treatment a therapeutically effective amount of the pharmaceutical composition of claim 14.

20. The method of claim 19 wherein the disease is osteoporosis.

21. The method of claim 20 wherein the patient is a human.

* * * * *